(12) United States Patent
Clemens et al.

(10) Patent No.: US 9,682,867 B2
(45) Date of Patent: Jun. 20, 2017

(54) NON-OXIDIZER PARTICLES

(71) Applicant: SOLVAY SA, Brussels (BE)

(72) Inventors: Joerg Clemens, Rheinbrohl (DE); Jürgen H. Rabe, Rheinbrohl (DE)

(73) Assignee: Solvay SA, Brussels (BE)

(*) Notice: Subject to any disclaimer, the term of this patent is extended or adjusted under 35 U.S.C. 154(b) by 0 days.

(21) Appl. No.: 14/892,803

(22) PCT Filed: May 21, 2014

(86) PCT No.: PCT/EP2014/060405
§ 371 (c)(1),
(2) Date: Nov. 20, 2015

(87) PCT Pub. No.: WO2014/187845
PCT Pub. Date: Nov. 27, 2014

(65) Prior Publication Data
US 2016/0096737 A1    Apr. 7, 2016

Related U.S. Application Data

(60) Provisional application No. 61/827,060, filed on May 24, 2013.

(30) Foreign Application Priority Data

Dec. 16, 2013 (EP) .................................. 13197512

(51) Int. Cl.
| | | |
|---|---|---|
| C01B 15/04 | (2006.01) | |
| C01B 15/043 | (2006.01) | |
| C01F 11/02 | (2006.01) | |
| A21D 2/02 | (2006.01) | |
| C01C 1/24 | (2006.01) | |
| A61K 8/22 | (2006.01) | |
| A61K 8/23 | (2006.01) | |
| A61K 8/26 | (2006.01) | |
| A61Q 5/08 | (2006.01) | |
| A61Q 11/00 | (2006.01) | |
| A61Q 19/00 | (2006.01) | |
| C10M 103/06 | (2006.01) | |
| C22C 1/06 | (2006.01) | |
| A61K 8/02 | (2006.01) | |

(52) U.S. Cl.
CPC ............... *C01F 11/02* (2013.01); *A21D 2/02* (2013.01); *A61K 8/0241* (2013.01); *A61K 8/22* (2013.01); *A61K 8/23* (2013.01); *A61K 8/26* (2013.01); *A61Q 5/08* (2013.01); *A61Q 11/00* (2013.01); *A61Q 19/00* (2013.01); *C01C 1/24* (2013.01); *C10M 103/06* (2013.01); *C22C 1/06* (2013.01); *C01B 15/043* (2013.01)

(58) Field of Classification Search
CPC .................................................. C01B 15/043
See application file for complete search history.

(56) References Cited

U.S. PATENT DOCUMENTS

| | | | |
|---|---|---|---|
| 3,118,798 A | 1/1964 | Winckler | |
| 3,402,155 A * | 9/1968 | Kutch ..................... C08L 81/00 | 524/292 |
| 4,101,644 A | 7/1978 | Ballou et al. | |
| 4,293,426 A | 10/1981 | Gago | |
| 4,490,274 A | 12/1984 | Maslyaev et al. | |
| 4,976,955 A | 12/1990 | Libin | |
| 5,741,427 A | 4/1998 | Watts et al. | |
| 6,193,776 B1 | 2/2001 | Doetsch et al. | |
| 6,319,328 B1 | 11/2001 | Greenberg et al. | |
| 2003/0049212 A1* | 3/2003 | Robinson ................. A61K 8/06 | 424/59 |
| 2005/0163729 A1 | 7/2005 | Zaidel et al. | |
| 2007/0128129 A1* | 6/2007 | Stehr ....................... A61K 8/66 | 424/50 |
| 2007/0166339 A1* | 7/2007 | Gupta ..................... A61K 8/22 | 424/401 |
| 2010/0317557 A1* | 12/2010 | Rabe ..................... C01B 15/106 | 510/218 |
| 2014/0349897 A1* | 11/2014 | Dobson, Jr. ............ C09K 8/035 | 507/211 |

FOREIGN PATENT DOCUMENTS

| | | |
|---|---|---|
| CN | 1136772 A | 11/1996 |
| CN | 1933800 A | 3/2007 |
| CN | 102641744 A | 8/2012 |
| CN | 102863931 A | 1/2013 |
| CN | 102943004 A | 2/2013 |
| EP | 0002543 A1 | 6/1979 |
| JP | 6427686 A | 1/1989 |
| JP | 6475407 A | 3/1989 |
| JP | 08301605 A | 11/1996 |
| JP | H08-301605 A | 11/1996 |

(Continued)

OTHER PUBLICATIONS

M Villarba. "Chapter 19: Electrochemistry: The Quest for Clean Energy." http://seattlecentral.edu/faculty/mvillarba/CHEM162/Chapter19.pdf, accessed May 2, 2016, pp. 1-24.*

GP Chandra Rao, S Satyaveni, A Ramesh, K Seshaiah, KSN Murthy, NV Choudary. "Sorption of cadmium and zinc from aqueous solutions by zeolite 4A, zeolite 13X and bentonite." Journal of Environmental Management, vol. 81, 2006, pp. 265-272.*

(Continued)

*Primary Examiner* — Isaac Shomer
(74) *Attorney, Agent, or Firm* — Osha Liang LLP

(57) ABSTRACT

Particles containing a strong oxidizer (classified as PG I according to the standard test method of the UN Manual of Tests and Criteria, 5$^{th}$ revised Edition, sub-section 34.4.1) and at least one other constituent, the amount and nature of the constituent(s) other than the strong oxidizer in the particles being such that the particles are classified as non-oxidizer according to the standard test method of the UN Manual of Tests and Criteria, 5$^{th}$ revised Edition, sub-section 34.4.1. Process for the production of these particles.

8 Claims, No Drawings

(56) References Cited

FOREIGN PATENT DOCUMENTS

| KR | 20080039088 A | 5/2008 | | |
|---|---|---|---|---|
| RU | 2209647 C2 | 8/2003 | | |
| WO | 9609244 A1 | 3/1996 | | |
| WO | WO 9609244 A1 * | 3/1996 | .............. | B01J 19/24 |
| WO | 2008080905 A1 | 7/2008 | | |
| WO | 2009083512 A1 | 7/2009 | | |

OTHER PUBLICATIONS

United Nations Manual of Tests and Criteria, 2009, 5th revised Edition, Subsection 34.4.1, Test methods for oxidizing substances, pp. 319-401; 83 pgs.

Office Action issued in Chinese Application No. 201480029750X; Dated Oct. 10, 2016 (14 pages).

* cited by examiner

NON-OXIDIZER PARTICLES

This application is a U.S. national stage entry under 35 U.S.C. §371 of International Application No. PCT/EP2014/060405 filed May 21, 2014, which claims priority to U.S. application No. 61/827,060 filed on 24 May 2013, and European application No. 13197512.0 filed on 16 Dec. 2013, and the whole content of each of these applications is hereby incorporated herein by reference for all purposes.

The present invention generally is related to particles being classified as non-oxidizer according to the standard test method for oxidizing solids of the UN Manual on Tests and Criteria for the Transport of Dangerous Goods, $5^{th}$ revised Edition, sub-section 34.4.1.

Calcium peroxide ($CaO_2$) is well known for its strong oxidizing properties and is therefore namely used in dough conditioning, soil remediation or amendment, water treatment, seed coating and toothpastes or other cosmetic formulations.

However, in many of these applications, magnesium peroxide ($MgO_2$) can be used as well and commercial formulations thereof offer the advantage of not being classified as hazardous for transport, while this is not the case for commercial formulations of $CaO_2$, which are generally classified as strong oxidizers (Class 5—Oxidizing Substances/Division 5.1, PG I acc. to REACH) according to the above mentioned test method of the UN Manual and must be labelled and handled accordingly. On the other hand, commercial grades of $CaO_2$ are generally cheaper than their $MgO_2$ equivalents (in terms of oxidizing power) namely because their raw materials are cheaper and their manufacturing process as well.

Patent application WO 2008/080905 in the name of the applicant teaches how to solve the oxidizer related hazard problem, but for another chemical than $CaO_2$, namely: for sodium percarbonate (PCS) which is not a strong oxidizer but a medium oxidizer (classified as PG II according to the above UN test method) or a weak oxidizer (classified as PG III). The solution set forth in this document is to mix/treat (blend or co-granulate) the particles with given additives among which sodium carbonate and bicarbonate. As will be shown later on, this solution merely transposed to the case of $CaO_2$ or any other strong oxidizer like ammonium persulfate for instance, does not solve the problem. In fact, any simple dilution of $CaO_2$, ammonium persulfate (($NH_4)_2S_2O_8$) or the like by any component does not solve the problem due to their strong oxidizing potential in comparison with the one of PCS. While using sodium bicarbonate seems to solve the problem indeed, the fact of having to blend or to co-granulate the additive implies an additional process step, which is time and money consuming.

An aim of the present invention is to provide new $CaO_2$, $((NH_4)_2S_2O_8$ or any other comparable strong oxidizing particles presenting reduced packaging, handling, storage, and/or transportation constraints versus those generally associated with such known oxidizing products, i.e. being no longer classified as oxidizers so no longer falling under Division 5.1. Another aim of the present invention is to provide new $CaO_2$ particles having besides the advantage of being manufactured in a simple and economic way.

Consequently, in a first aspect, the present invention concerns particles containing a strong oxidizer (classified as PG I according to the standard test method of the UN Manual of Tests and Criteria, $5^{th}$ revised Edition, sub-section 34.4.1, like $CaO_2$ or $(NH_4)_2S_2O_8$ for instance) and at least one other constituent, the amount and nature of the constituent(s) other than the strong oxidizer in the particles being such that the particles are classified as non-oxidizer according to the standard test method of the UN Manual of Tests and Criteria, $5^{th}$ revised Edition, sub-section 34.4.1.

More particularly, in a first aspect, the invention concerns particles containing $CaO_2$ or $(NH_4)_2S_2O_8$ (or a similar strong oxidizer) and at least one other constituent, the amount and nature of this constituent(s) in the particles being such that when the strong oxidizer decomposes, said constituent generates water and/or a gas in an amount appropriate to modify the burn rate and/or to absorb at least partially the decomposition heat of the strong oxidizer so that the particles are classified as non-oxidizer according to the standard test method of the UN Manual of Tests and Criteria, sub-section 34.4.1.

In other words: the invention concerns particles containing $CaO_2$ or a similar strong oxidizer and at least one other constituent, the amount and nature of which being such that when the decomposition of the strong oxidizer boosts any combustion by related oxygen release, preferably water and/or a gas like CO2 (which act as a burn rate modifier in a suffocative manner) is generated be the other constituent(s) in an amount appropriate to inhibit at least partially the progress of the combustion or in other words: to impact the burning rate so that the particles are classified as non-oxidizer according to the standard test method of the UN Manual of Tests and Criteria, sub-section 34.4.1.

In the above, by "generate" is meant that the constituent(s) other than the strong oxidizer in fact liberate water/gas before or at the same time as when the strong oxidizer is decomposing. Preferably, these constituent(s) have a thermal decomposition temperature (i.e. the temperature at which their thermal decomposition begins) below or equal to that of CaO2 (or $(NH_4)_2S_2O_8$ or comparable).

In the frame of the invention, the term "particles" is meant to designate a powder or granule or multi-layer tablet (etc.) made of free particles, preferably with a low moisture content (typically below 1%).

Within the frame of the invention, although these particles are classified as non-oxidizers from an hazard point of view, they nevertheless have oxidizing properties and namely, a content of available oxygen (AvOx) which is preferably of at least 1%, more preferably at least 4.0% by weight and even more preferably, at least 6.0% by weight, as required or desired for their intended use. Generally however, this AvOx content is lower than 11.0% by weight, even lower than 10.0% by weight, and more preferably, lower than 9.0% by weight, or even than 8.0%. This AvOx content can be adapted by controlling the composition of the particles i.e. the respective amount of the strong oxidizer and of the other constituent(s) but its maximum value depends on the nature thereof: see below. The content of available oxygen is measured by titration with potassium permanganate after dissolution in sulphuric acid (see ISO standard 1917-1982). Generally, and Avox content between 6.0 and 9.0% by weight is obtained with commercial grades of CaO2.

According to the invention, the other constituent(s) of the particles are in an amount and of a nature such that they are able to generate water and/or a gas in an amount and in a temperature range appropriate to impact the speed of combustion (and/or to absorb at least partially the decomposition heat of the strong oxidizer, although this effect is generally less efficient). According to the invention, this means that the amount of water and/or gas generated during the above mentioned UN 0.1 test is enough to bring the burning time according to said test above a given reference value i.e. 120 seconds. In that regard, the reference data used herein to classify solid oxidizers is linked to test results of the hazard laboratory in charge at SOLVAY and may differ to other UN 0.1 tests results in comparison in an absolute manner. According to SOLVAY results, for weak oxidizers (classified as 5.1 PGIII), the burning time is namely comprised between 120 and 50 seconds, for medium oxidizers (classified as 5.1 PGII), it is between 50 and 10 seconds, and it is less than 10 seconds for strong oxidizers (classified as 5.1 PGI). On the other hand, particles with a burning time above 120 seconds are classified as non-oxidizers.

In a preferred embodiment, the strong oxidizer is CaO2. TG (thermogravimetric) analysis of $CaO_2$ (namely: of the commercial grade available under the trade name IXPER® 75C from Solvay Chemicals, and which contains an average of 75% by weight of $CaO_2$) has namely shown that this product releases oxygen (which is a combustion booster) between 200 and 350° C. under normal atmospheric conditions, in an open system. The number in mentioned IXPER® tradename reflects the average content of industrially produced IXPER® grades, e.g. IXPER®75C or IXPER®30C represents IXPER grades containing 75% or 30% by mass of calcium peroxide on the average.

It has now been found that this range is the ideal range in which or below which the "diluent(s)" (constituent(s) other than $CaO_2$) should release water and/or a gas. More specifically, it has been found that substances which release water and/or gas at a temperature above ambient (for instance, above 50° C. or even, above 60° C.) but below 350° C. give good results.

Examples of such substances are molecular sieves, preferably of the zeolite type (hydrated alumino-silicates), aluminium or magnesium hydroxide, and basic magnesium carbonate hydrates. Among zeolites, those of the type A, X, Y, L, more precisely of the type 3A, 4A, 5A, 10X and 13X or any comparable grade like mordenite can be used. Zeolites of the type 13X as an example give good results within the tested frame of the invention. Aluminium hydroxide as well as basic magnesium carbonate monohydrate are particularly efficient. Aluminium hydroxide is particularly preferred.

Other examples of such substances are hydrates of salts of a metal like Na, K, Ca, Mg and Al; and bicarbonates like sodium bicarbonate.

The latter has the advantage of being cheap and of releasing both water and CO2 on decomposition below 200° C. so that it is very effective in reducing the speed of decomposition of CaO2. It is also a pH buffer and it is besides environmental friendly.

For the same reasons, the use of sodium bicarbonate is also advantageous for rendering ammonium persulfate non oxidizer.

There are several methods for manufacturing the particles according to the invention.

In a first embodiment, a commercially available grade of $CaO_2$ or $(NH_4)_2S_2O_8$ (or a similar strong oxidizer) is mixed with the at least one other constituent. In particular, the above mentioned commercial grade IXPER® 75C can be used and for instance be mixed with at least 40% of diluent (in weight based on the total weight of the particles), preferably with at least 50% in weight of diluent, or even with up to 60% diluent, depending on its nature.

In this embodiment, sodium bicarbonate is preferred. Mixed with commercial grade IXPER® 75C in an amount of 50% (in weight based on the total weight of the particles), sodium bicarbonate namely allows reaching an UN 0.1 test burning time of above 180 sec. Similar results can be obtained with ammonium persulfate.

Metal salt hydrates also give good results in this embodiment and more particularly, Mg sulphate heptahydrate. Like sodium bicarbonate, mixed with commercial grade IXPER® 75C in an amount of 50% (in weight based on the total weight of the particles), this substance also allows reaching an UN 0.1 test burning time of above 180 sec. Another metal salt hydrate allowing to reach the same result is tri-sodium citrate pentahydrate.

Since commercial $CaO_2$ is rarely pure but instead, comprises other constituents (which may be diluents as well, or inert substances (not emitting water at least in the required temperature range) like $Ca(OH)_2$ or other inorganic calcium compounds for instance), the $CaO_2$ concentration of the particles with these dilution ratios is generally below 60, 50, and 40% respectively. It generally is of not more than 45% in weight (based on the total weight of the particles), preferably of not more than 40% and even more preferably, of not more than 37.5% in weight. Sometimes, it may even be below 30% in weight.

These concentrations correspond respectively to theoretical AvOx values for the $CaO_2$ particles of 9.9%, 8.8%, 8.3%, and 6.6% (calculated according to the formula 0.22*concentration in w %, where 0.22 corresponds to the molecular weight of $O_2$ (16) divided by the molecular weight of $CaO_2$ (72)). In fact, the maximum content of available oxygen (AvOx) of the $CaO_2$ particles to stay below the classification as 5.1 material is depending to some extent on the nature of the additive(s), as will be shown in the examples below.

In a second embodiment, the strong oxidizer is CaO2 and the diluent may be introduced in the $CaO_2$ particles during the manufacture thereof. Generally, $CaO_2$ is manufactured by adding hydrogen peroxide ($H_2O_2$) to slaked lime (slurry of $Ca(OH)_2$ in water) to form crystals of $CaO_2$, which are then dried and finally packaged. Hence, according to that embodiment, the diluent(s) may be introduced in the slaked lime before reaction with the $H_2O_2$; after said reaction and just before drying; or after drying prior to packaging the particles. Preferably, it is introduced after said reaction and just before drying. This embodiment allows a simple and economic manufacturing route but requires that the diluent does not release (at least all or too much of) its water or gas during said drying.

In this embodiment, magnesite and aluminium hydroxide give good results and more particularly, aluminium hydroxide. It has namely been found that aluminium hydroxide does not alter the crystallisation behaviour of the CaO2, which may happen with other constituents for instance if the slurry to be dried is stored before said drying while already containing the diluent.

The present invention also concerns the use of the above described calcium peroxide or ammonium persulfate (or similar strong oxidizer) particles:

in environmental applications, namely to accelerate the natural attenuation of contaminated soils;
for the treatment of grease traps namely to help reduce sulfide-based odors;
for oxygenating the lower parts of artificial or natural lakes as well as wastewater and effluent;
in oil field applications, namely as polymer breaker;
for soil amendment in agricultural, horticultural, and forestry applications;
in the baking industry, namely as component of dough conditioners;
in personal and oral care applications;
in hair care applications, namely as ingredient of bleaching compositions;

as curing agent in some sealant compositions, namely one-part polysulfide-based anhydrous sealants;

in metallurgy, namely as a source of oxygen in aluminothermic processes.

In particular for environmental applications, the present invention relates to methods for treating or cleaning a contaminated material such as soil and/or water comprising utilizing the above described calcium peroxide particles. The contaminated material to be treated or cleaned may be subterranean or on the surface. The above described calcium peroxide particles are generally used to accelerate the natural attenuation of the contaminated material.

The material is generally contaminated with organic contaminants, such as hydrocarbons and/or halogenated compounds, in particular halogenated hydrocarbons. For example, soil contaminants that can be effectively treated by such method include petrochemicals, chlorinated organics, pesticides, energetics, perchlorates, etc.

The method for cleaning or treating a contaminated material may include chemical oxidation or assisted bioremediation or both of at least one contaminant in the contaminated material in the presence of above described calcium peroxide particles to remove at least a portion of such contaminant from the material.

The term "assisted bioremediation" is intended to denote enhancing the growth of aerobic microorganisms by supplying them with oxygen, thereby allowing them to multiply faster leading to an increased rate of degradation of the contaminant(s).

The method for chemical oxidation and/or assisted bioremediation of the contaminated material generally comprises contacting the contaminated material with at least the above described calcium peroxide particles.

Contacting can be accomplished in any manner, for example by introducing the solid particles or slurry (particles suspended in a liquid) in or onto the contaminated material to be treated in any manner known in the art.

The $CaO_2$ peroxide compound is preferably added as a slurry. Preferred concentrations for $CaO_2$ peroxide particles are for instance between about 20% by weight and about 35% by weight. The slurry could be more dilute (less than 20% by weight of particles) if the solid contaminated material being treated is very porous.

Alternatively, the peroxide compound can be added as solid particles. They could be used in a soil remediation application as a solid mixed with the soil.

The chemical oxidation reaction would proceed as a result of the slow release of $H_2O_2$ from the above described calcium peroxide particles. The calcium peroxide also may generate oxygen for long-term assisted bioremediation.

With regard to treatment, the amount of the peroxide compound applied to the contaminated material being treated is not limited, and can range for example from a ratio of from 0.0001 to 10,000 (of the above described calcium peroxide particles in pounds (lbs)/cubic feet of material being treated). A generally useful range for such ratio is from 0.01 to 1.5, for example from 0.2 to 1. A preferred range of dosing is up to 2,000 mg/L.

In embodiments according to the invention, the method of use further includes the use of at least one metal chelate, especially transition metal chelate, such as a Fe chelate, either as such, or in the form of the metal salt (e.g., ferrous or ferric salt) and a separate ligand (all of which are hereinafter referred to as "metal chelate"). The metal chelate can either be added together with $CaO_2$ peroxide particles or slurry, or separate injections or additions to the material being treated may be made whereby the particles or slurry of $CaO_2$ peroxide or slurry are or is added before, during, or after the metal chelate.

Alternatively, the chelating agent may be added to the material being treated (e.g., soil) in order to chelate with metals such as Fe in the ground. A buffer can be also added either in the peroxide particles or slurry, or with the metal chelate to adjust the pH, preferably to 7-9. Preferred transition metals other than Fe include Mn and Cu, and are in particular those capable of generating OH radicals from $H_2O_2$.

The relative amount of the above described calcium peroxide particles and metal chelate are not limited. The molar ratio of metal chelate to $CaO_2$ peroxide is generally from 0.01 to 10 of metal chelate/peroxide. Such ratio is preferably less than 1 and/or more than 0.05, or even more than 0.1, or even more than 0.2, or even more than 0.3, etc.

Optionally, in some embodiments according to the invention, the method of use further includes adding products that are considered nutrients to microbes either separately or in combination with other products to the peroxide particles or slurry. As appropriate, some of these optional products may be injected or mixed in their dry form. Metal chelates described in U.S. Pat. No. 5,741,427 and U.S. Pat. No. 6,319,328 can be used herein. A preferred metal is Fe. Preferred chelating agents (ligands) include EDTA, citric acid, nitrilotriacetic acid, EDTA acid types, diethylenetriaminepentaacetic acid, hydroxyethylenediaminetriacetic acid, methylglycinediacetic acid, phosphonates, and the TRILON® chelating agents of BASF, all of which being incorporated herein by reference.

The invention will now be illustrated by the Examples and Counter-examples below, the aim of which is merely to detail some specific aspects of the invention and not to limit its scope thereto.

Tables 1 to 4 below show the results of the above mentioned burning test UN O.1 applied to some commercial grades of IXPER® peroxides, eventually diluted with another component (if and as indicated) in a ratio 4:1 of solid to cellulose to demonstrate its natural oxidizing power.

With the exception of sample IXPER® 70CG (with the G for granules), all diluents were reduced to fine powders of less than 500 μm before performing the test. IXPER® 70CG shows no fines/particle sizes below 500 μm and was tested as delivered.

In case of blending procedures of solid oxidizers with mentioned additives, latter were mechanically milled to a similar range of spectrum of particle sizes of solid oxidizer to minimize risk of segregation during handling, storage or transport. All ingredients were then thoroughly mixed within a RHÖNRAD mixer.

TABLE 1

| Raw IXPER ® material | $t_{O.1}$ [s]: | Class. |
|---|---|---|
| IXPER75C (03.06.10) – w(CaO2) = 75.9% | 10 | 5.1, I |
| IXPER60C (03.07.08) – w(CaO2) = 61.4%. | 48 | 5.1, II |
| IXPER70CG (16.07.2010) – w(CaO2) = 72.0% | 20 | 5.1, II |
| IXPER35M (16.07.2010) – w(MgO2) = 38.7% | 178 | not 5.1 |

Time References (KBrO₃)

| $t_{O.1}$ [s]: | Result |
|---|---|
| 120 | 5.1, PGIII |
| 50 | 5.1, PGII |
| 10 | 5.1, PGI |

TABLE 2

| IXPER 60 ®C + calcium carbonate | $t_{O.1}$ [s]: Class. |
|---|---|
| IXPER60C + CaCO₃ – w(CaO₂) = 20.2% – 13.07.2010 | 81  5.1, III |
| IXPER60C + CaCO₃ – w(CaO₂) = 30.1, % – 13.07.2010 | 46  5.1, II |
| IXPER60C + CaCO₃ – w(CaO₂) = 40.5, % – 13.07.2010 | 16  5.1, II |

TABLE 3

| IXPER75 ®C + calcium hydroxide | $t_{O.1}$ [s]: Class. |
|---|---|
| 75C with Ca(OH)₂ (08.06.2010) – w(CaO₂) = 20.1% | 96  5.1, III |
| 75C with Ca(OH)₂ (08.06.2010) – w(CaO₂) = 30.4% | 57  5.1, III |
| 75C with Ca(OH)₂ (08.06.2010) – w(CaO₂) = 40.4% | 22  5.1, II |
| 75C with Ca(OH)₂ (08.06.2010) – w(CaO₂) = 50.0% | 14  5.1, II | zeolite 13X powder and magnesium hydroxide need to be present in an amount of at least 50% in weight (see Table 4).

For all the diluents tested in Table 4, a TG analysis was performed between ambient temperature and 900° C. as a maximum in order to detect the temperatures at which they release gases (mainly steam or carbon dioxide due to thermal decomposition). The results are shown in Table 5 below.

The conditions of this TG test were the following: 70 µl Alumina crucible with lid; ~30 mg sample; dry air; air flow through oven: 20 ml/min; heat rate: 3 to 5 K/min; temp range: 25° C. to max 900° C.

TABLE 5

| Diluent | Decomposition Formula | Temp Range of Water/Gas Release [° C.] |
|---|---|---|
| Zeolite 13X powder | Na₂O × Al₂O₃ × 2.5 SiO₂ × n H₂O | 20-400 |
| Ca(OH)₂ | Ca(OH)₂ → CaO + H₂O | 350-500 |
| Al(OH)₃ | 2Al(OH)₃ → Al₂O₃ + 3H₂O | 200-650 |
| Mg(OH)₂ | Mg(OH)₂ → MgO + H₂O | 200-650 |
| Magnesite (alkaline MgCO3) | Mg(OH)₂ × Mg(CO₃) × 2H₂O → 2MgO + 3H₂O + CO₂ | 150-600 |
| IXPER75C | CaO₂ → CaO + ½O₂ | 250-350 |
|  | Ca(OH)2 → CaO + H2O | 350-450 |
|  | CaCO3 → CaO + CO2 | 550-750 |

TABLE 4

| | dilution substance | w(75C) [%] | w(CaO₂) [%] | $t_{0.1}$ [s] | Class TDG | w(75C) [%] | w(CaO₂) [%] | $t_{0.1}$ [s] | Class TDG | w(75C) [%] | w(CaO₂) [%] | $t_{0.1}$ [s] | Class TDG |
|---|---|---|---|---|---|---|---|---|---|---|---|---|---|
| substance: | calcium hydroxide | 24 | 18 | 129 | NOT 5.1 | confirmation of findings as reported in 100923.JCS.0 | | | | | | | |
| sample: | technical pure | | | | | | | | | | | | |
| supplier: | unkown | | | | | | | | | | | | |
| substance: | zeolite 13X powder | 40 | 30 | >180 | NOT 5.1 | 50 | 37.5 | 144 | NOT 5.1 | 55 | 41.3 | 86 | 5.1, PG III |
| sample: | 11-00071 | | | | | | | | | | | | |
| supplier: | Sud-Chemie | | | | | | | | | | | | |
| substance: | magnesium hydroxide | 40 | 29.6 | 139 | NOT 5.1 | 50 | 37.5 | 139 | NOT 5.1 | 60 | 45 | 69 | 5.1, PGIII |
| sample: | Lot.: STBB4230 | | | | | | | | | | | | |
| supplier: | SIGMA-ALDRICH | | | | | | | | | | | | |
| substance: | basic magnesium carbonate mono hydrate | 50 | 37.5 | >180 | NOT 5.1 | 60 | 45 | 120 | NOT 5.1 | due to borderline situation, no further tests | | | |
| sample: | Lot.: 87197MJ | | | | | | | | | | | | |
| supplier: | ALDRICH | | | | | | | | | | | | |
| substance: | aluminium hydroxide | 50 | 37.5 | >180 | NOT 5.1 | 60 | 45 | 163 | NOT 5.1 | 70 | 52.5 | 64 | 5.1, PGIII |
| sample: | K40978091 020 | | | | | | | | | | | | |
| supplier: | MERCK | | | | | | | | | | | | |

As can be seen from these tables:
- IXPER®35M is not classified as hazardous (Class 5—Oxidizing Substances/Division 5.1), while grades IXPER® 60C, 75C, and 75CG are (see Table 1);
- CaCO₃ and Ca(OH)₂ even used in rather big amounts (actually, the first example of Table 2 corresponds to approximately 65% in weight of CaCO₃ and the first example of Table 3 corresponds to approximately 75% in weight of Ca(OH)₂ are not efficient as diluents s according to the invention, while Mg(OH)₂ seems to be efficient at an amount of 74% (see Tables 2, 3, and 4);
- basic magnesium carbonate mono hydrate (magnesite) and aluminium hydroxide are already effective diluents at 40% in weight (for 60% in weight of IXPER® 75C, which corresponds to 45% in weight of CaO₂), while This table 5 shows that Ca(OH)₂, which is a poor diluent, has a decomposition onset above 350° C. (while CaO₂ releases oxygen roughly between 250 and 350° C.), while the other diluents of Table 4, which are good diluents, have an overlap between their decomposition temperature range and the one of CaO₂.

Additional trials were realized both by blending (I) and introducing during its manufacture and prior to its drying (II), sodium bicarbonate, magnesite, aluminium hydroxide and epsomite (hydrous magnesium sulfate mineral with formula MgSO4.7H2O) in CaO2.

The blending (I) was performed as described above. As to the introduction during CaO2 manufacture, it was in fact simulated as follows:

Normally, as described above, $CaO_2$ is manufactured by adding hydrogen peroxide ($H_2O_2$) to slaked lime (slurry of $Ca(OH)_2$ in water) to form crystals of $CaO_2$ in suspension in water, which are then dried. Here, a suspension of IXPER® 75C in water was used, to which the above mentioned diluents were added and finally, the mixtures were dried it in a spray drier at an average temperature of 110° C.

The results are shown in Tables 6 below, from which it appears that magnesite and aluminium hydroxide lead to products with a comparable behaviour when added during the manufacture of CaO2 as when blended therewith and are therefore suitable for introduction after reaction and before drying, while sodium bicarbonate and epsomite are not.

TABLE 6

| BLEND | Ratio 75C:Diluent | | | |
|---|---|---|---|---|
| | 40:60 30C | 50:50 38C | 60:40 45C | 70:30 53C |
| BICAR | NOT 5.1 | NOT 5.1 | 5.1 III | n.d. |
| Magnesite | NOT 5.1 | NOT 5.1 | 5.1 III | n.d. |
| AL(OH)$_3$ | NOT 5.1 | NOT 5.1 | NOT 5.1 | 5.1, III |
| Epsomite | NOT 5.1 | NOT 5.1 | 5.1, III | n.d. |

| SPRAY-DRYER (FEX) | Ratio 75C:Diluent | | |
|---|---|---|---|
| | 40:60 30C | 50:50 37C | 60:40 45C |
| BICAR | Decomposition (instantaneous gas evolution in suspension) | | |
| Magnesite | NOT 5.1 | NOT 5.1 | 5.1 III |
| AL(OH)$_3$ | NOT 5.1 | NOT 5.1 | 5.1 III |
| Epsomite | 5.1, III | n.d. | n.d. |

Finally, to check the stability of the suspension of CaO2 with the diluent, additional trials were performed using pure IXPER and IXPER:additive blends with a ratio of 1:1 as follows:

a) IXPER reference: IXPER75C at 75% $CaO_2$ by mass
b) Magnesite with IXPER mash: w($CaO_2$)~40% $CaO_2$ by mass
c) Al(OH)$_3$ with IXPER mash: w($CaO_2$)~39% $CaO_2$ by mass. The results in Table 7 show that Al(OH)$_3$ seems to lead to a more stable dispersion than magnesite.

TABLE 7

| Remaining time [h] | $CaO_2$ [%] IXPER Ref. Slurry | $CaO_2$ [%] IXPER Magnesite Slurry | $CaO_2$ [%] IXPER Al(OH)$_3$ Slurry |
|---|---|---|---|
| 0 | 75 | 40 | 39 |
| 4 | 75 | 21 | 38 |
| 6 | 73 | 20 | 37 |

Blends were also made in the same conditions as explained above, but using APS (ammonium persulfate) instead of CaO2. The results obtained are shown in Table 8 below.

TABLE 8

| Sample/Blend | ratio mix | $t_{O.1}$ [s] | Result |
|---|---|---|---|
| APS pur | 100:0 | 11 | 5.1, I |
| APS pur + Al(OH)$_3$ | 60:40 | 18 | 5.1, II |
| APS pur + Al(OH)$_3$ | 50:50 | 40 | 5.1, II |
| APS pur + Al(OH)$_3$ | 40:60 | 81 | 5.1, III |
| APS pur + Al(OH)$_3$ | 30:70 | >180 | NOT 5.1 |
| APS pur + basic magnesium carbonate mono hydrate | 60:40 | 73 | 5.1, III |
| APS pur + basic magnesium carbonate mono hydrate | 50:50 | >180 | NOT 5.1 |
| APS pur + magnesium hydroxide | 70:30 | 41 | 5.1, II |
| APS pur + magnesium hydroxide | 50:50 | 100 | 5.1, III |
| APS pur + magnesium hydroxide | 40:60 | >180 | NOT 5.1 |
| APS pur + magnesium hydroxide | 30:70 | >180 | NOT 5.1 |
| APS pur + sodium bicarbonate | 40:60 | >180 | NOT 5.1 |
| APS pur + sodium bicarbonate | 50:50 | >180 | NOT 5.1 |
| APS pur + sodium bicarbonate | 60:40 | 160 | NOT 5.1 |

As can be seen from Table 8, sodium bicarbonate is especially efficient in making APS non oxidizer.

Should the disclosure of any patents, patent applications, and publications which are incorporated herein by reference conflict with the description of the present application to the extent that it may render a term unclear, the present description shall take precedence.

The invention claimed is:

1. A process for the preparation of particles that comprise $CaO_2$, comprising:
   adding hydrogen peroxide to slaked lime to form crystals of $CaO_2$;
   adding at least one other constituent to the slaked lime, the other constituent selected from the group consisting of magnesite and aluminum hydroxide; and
   drying the $CaO_2$ crystals;
   wherein the at least one other constituent is added to the slaked lime either before the hydrogen peroxide, or after addition of hydrogen peroxide but before drying the $CaO_2$ crystals, and
   wherein the at least one other constituent is added in an amount effective to render the particles as non-oxidizers.

2. The process according to claim 1, wherein the at least one other constituent is aluminum hydroxide.

3. The process according to claim 1, wherein the particles are classified as non-oxidizer according to the standard test method of the UN Manual of Tests and Criteria, 5$^{th}$ revised Edition, sub-section 34.4.1.

4. The process according to claim 1, wherein the particles have a content of available oxygen between 6.0% and 9.0% by weight.

5. The process according to claim 2, wherein the aluminum hydroxide does not alter the crystallization behavior of the $CaO_2$.

6. A process for the preparation of particles that comprise $CaO_2$, comprising:
   adding hydrogen peroxide to slaked lime to form crystals of $CaO_2$;
   adding at least one other constituent to the slaked lime, the other constituent selected from the group consisting of magnesite and aluminum hydroxide; and
   drying the $CaO_2$ crystals,
   wherein the at least one other constituent is added to the slaked lime either before the hydrogen peroxide, or after addition of hydrogen peroxide but before drying the $CaO_2$ crystals, and
   wherein the at least one other constituent is added in an amount effective to render the particles to be classified as non-oxidizer according to the standard test method of the UN Manual of Tests and Criteria, 5$^{th}$ revised Edition, sub-section 34.4.1, and, wherein the particles have a content of available oxygen between 6.0% and 9.0% by weight.

7. The process according to claim 6, wherein the at least one other constituent is aluminum hydroxide.

8. The process according to claim 7, wherein the aluminum hydroxide does not alter the crystallization behavior of the $CaO_2$.

* * * * *